United States Patent
Kaji (10) Patent No.: US 8,043,492 B2
(45) Date of Patent: Oct. 25, 2011

(54) METHOD FOR PRETREATMENT OF ELECTROPHORESIS, SUBSTRATE FOR ANALYSIS, AND PRETREATMENT APPARATUS FOR ELECTROPHORESIS

(75) Inventor: Toru Kaji, Kyoto (JP)

(73) Assignee: Shimadzu Corporation, Kyoto (JP)

(*) Notice: Subject to any disclaimer, the term of this patent is extended or adjusted under 35 U.S.C. 154(b) by 223 days.

(21) Appl. No.: 12/300,788

(22) PCT Filed: May 26, 2006

(86) PCT No.: PCT/JP2006/310522
§ 371 (c)(1),
(2), (4) Date: Nov. 13, 2008

(87) PCT Pub. No.: WO2007/138654
PCT Pub. Date: Dec. 6, 2007

(65) Prior Publication Data
US 2009/0223822 A1 Sep. 10, 2009

(51) Int. Cl.
G01N 27/447 (2006.01)
B01D 57/02 (2006.01)

(52) U.S. Cl. ................................................. 204/453

(58) Field of Classification Search .......... 204/450–455, 204/600–604
See application file for complete search history.

(56) References Cited

U.S. PATENT DOCUMENTS

2002/0182749 A1* 12/2002 Singh et al. ............... 436/514
2005/0148091 A1* 7/2005 Kitaguchi et al. .......... 436/164

FOREIGN PATENT DOCUMENTS

| JP | 10-010088 A | 1/1998 |
| JP | 2002-148236 A | 5/2002 |
| JP | 2002-310858 A | 10/2002 |
| JP | 2002-310990 A | 10/2002 |
| JP | 2003-4700 A | 1/2003 |
| JP | 2003-166975 A | 6/2003 |
| WO | WO-2005/029062 A2 | 3/2005 |

OTHER PUBLICATIONS

Huang, X., et al., "Current-Monitoring Method for Measuring the Electroosmotic Flow Rate in Capillary Zone Electrophoresis", Analytical Chemistry, vol. 60, 1988, p. 1837-1838.*
International Search Report for the Application No. PCT/JP2006/310522 mailed Aug. 15, 2006.
Notification of Reasons for Refusal for the Application No. 2008-517718 from Japan Patent Office mailed Oct. 26, 2010.

* cited by examiner

Primary Examiner — Jeffrey T Barton
Assistant Examiner — J. Christopher Ball
(74) Attorney, Agent, or Firm — Cheng Law Group, PLLC

(57) ABSTRACT

A sample (14) is supplied into a sample reservoir (8) (see (A)). A voltage is applied by an electrode (20) to introduce the sample into a capillary (6) filled with a separation medium (see (B)). A liquid (16) for replacement having a larger specific gravity than the sample (14) is supplied into the sample reservoir (8), and the sample (14) remaining in the sample reservoir (8) is replaced with the liquid (16) for replacement (see (C)).

5 Claims, 9 Drawing Sheets

Elapsed time from beginning of measurement

METHOD FOR PRETREATMENT OF ELECTROPHORESIS, SUBSTRATE FOR ANALYSIS, AND PRETREATMENT APPARATUS FOR ELECTROPHORESIS

TECHNICAL FIELD

The present invention relates to a method for analyzing a trace amount of protein, nucleic acid, drug, or the like in, for example, biochemical, molecular biological and clinical fields. More particularly, the present invention relates to electrophoretic analysis using a substrate for analysis such as a microchip or a capillary plate.

BACKGROUND ART

An electrophoresis apparatus has been conventionally used for analysis of a trace amount of protein, nucleic acid, or the like. A typical example of such an electrophoresis apparatus includes a capillary electrophoresis apparatus using a capillary tube. However, such an apparatus using a capillary tube requires complicated handling. Therefore, in order to facilitate the handling of the apparatus and to achieve an increase in the speed of analysis and a reduction in the size of the apparatus, various substrates for analysis such as a microchip formed by providing a capillary in a substrate and a capillary plate formed by providing a plurality of capillaries in one plate have been proposed and used (see Patent Documents 1 and 2).

In such a substrate for analysis, a capillary formed therein is used as a separation channel for electrophoresis or a column for liquid chromatography. The capillary has both ends open at the surface of the substrate, and an opening provided at one of the ends of the capillary serves as a reservoir for injecting a sample.

Electrophoresis using a substrate for analysis involves a sample introduction step as pretreatment for analysis. As one pretreatment method, an electrokinetic injection method can be mentioned. According to this method, a sample is injected into a reservoir in a state where a capillary is filled with a separation medium, a voltage is then applied through an electrode to introduce the sample into the capillary, the reservoir is then washed and filled with a buffer solution, and a voltage is then applied through an electrode to carry out electrophoretic analysis of the sample.

Patent Document 1: Japanese Patent Application Laid-open No. 2002-310990

Patent Document 2: Japanese Patent Application Laid-open No. 2003-166975

DISCLOSURE OF THE INVENTION

Problems to be Resolved by the Invention

If the end surface of the separation medium charged in the capillary, facing the reservoir, is disturbed by washing carried out after sample introduction, there is a problem that band formation is affected and separation performance is degraded. Therefore, washing of the reservoir before analysis is carried out by, for example, repeatedly sucking and discharging a liquid such as a buffer solution in the reservoir by way of a nozzle in such a manner that the end surface of the capillary is not disturbed. In this case, however, it is difficult to sufficiently wash the reservoir without disturbing the reservoir-side end surface of the capillary. Further, when the reservoir is washed to the extent that the reservoir-side end surface of the capillary is not disturbed, a sample remains near the reservoir-side end surface of the capillary. If the sample is in contact with the reservoir-side end surface of the capillary, the sample remaining in the reservoir is introduced into the capillary during electrophoretic analysis, thereby causing a problem that a signal resulting from the remaining sample appears as a background.

It is therefore an object of the present invention to make it possible, in electrophoretic analysis using a substrate for analysis, to remove a sample remaining near the reservoir-side end surface of a capillary without disturbing the reservoir-side end surface of the capillary after the sample is introduced into the capillary from a reservoir.

Means of Solving the Problems

The present invention is directed to a method for pretreatment of electrophoretic analysis using a substrate for analysis having a capillary for separating a sample and a reservoir provided at the end portion of the capillary to introduce a sample into the capillary, the method including, after a sample introduction step in which a sample is supplied into the reservoir and then a voltage is applied to introduce the sample into the capillary but before an electrophoretic separation step in which the sample is subjected to electrophoretic separation, a sample replacement step in which a liquid for replacement having a larger specific gravity than the sample is introduced into the reservoir to remove the sample remaining in the reservoir from the reservoir.

In a case where, in the sample introduction step, a buffer solution is supplied into the reservoir prior to the supply of a sample into the reservoir, the sample to be supplied into the reservoir is preferably a sample solution using, as a solvent, a liquid having a larger specific gravity than the buffer solution.

Further, in a case where the substrate for analysis has a solution supply channel for supplying a solution from the side of the reservoir, the sample may be introduced through the solution supply channel in the sample introduction step of the pretreatment method according to the present invention, and/or the liquid for replacement may be introduced through the solution supply channel in the sample replacement step.

The present invention is also directed to a substrate for analysis having a capillary for separating a sample and a reservoir provided at the end portion of the capillary to introduce a sample into the capillary, the substrate including a solution supply channel for supplying a solution from the side of the reservoir.

The present invention is also directed to a pretreatment apparatus for electrophoresis comprising: a substrate holding unit for holding a substrate for analysis having a capillary for separating a sample and a reservoir provided at the end portion of the capillary to introduce a sample into the capillary; a sample supply unit for supplying a sample into the reservoir of the substrate; a buffer solution supply unit for supplying a buffer solution into the reservoir of the substrate; a sample introduction system having an electrode for applying a voltage so that the sample supplied into the reservoir by the sample supply unit is introduced into the capillary; and a liquid for replacement supply unit for supplying a liquid for replacement having a larger specific gravity than the sample into the reservoir after the sample is introduced into the capillary by the sample introduction system.

One example of a sample suitable for use in the pretreatment apparatus for electrophoresis according to the present invention is a sample solution using, as a solvent, a liquid having a larger specific gravity than the buffer solution to be supplied by the buffer solution supply unit. In this case, the sample supply unit preferably supplies the sample solution into the reservoir after the buffer solution supply unit supplies the buffer solution into the reservoir.

In a case where the substrate held by the substrate holding unit has a solution supply channel for supplying a solution from the side of the reservoir, the sample supply unit may supply the sample solution into the reservoir through the solution supply channel. In this case, the liquid for replacement supply unit may also supply the liquid for replacement into the reservoir through the solution supply channel.

EFFECTS OF THE INVENTION

Since the pretreatment method according to the present invention includes, after a sample introduction step in which a sample is supplied into a reservoir and then a voltage is applied to introduce the sample into a capillary but before an electrophoretic separation step in which the sample is subjected to electrophoretic separation, a sample replacement step in which a liquid for replacement having a larger specific gravity than the sample is introduced into the reservoir to remove the sample remaining in the reservoir from the reservoir, it is possible to remove the sample remaining in the reservoir from the reservoir without disturbing the reservoir-side end surface of the capillary and thereby to prevent the degradation of separation performance and improve the background of a signal.

Further, in the sample introduction step, by supplying a buffer solution into the reservoir prior to the supply of a sample into the reservoir and then by supplying, as the sample, a sample solution using, as a solvent, a liquid having a larger specific gravity than the buffer solution into the reservoir, it is possible to carry out sample introduction into the capillary while preventing the sample from being dried. According to this method, after the sample solution is introduced into the capillary, the reservoir is in a state where it is filled with the buffer solution, but by introducing a liquid for replacement having a larger specific gravity than the sample solution into the reservoir, the sample solution remaining in the reservoir can be replaced with the liquid for replacement due to their difference in specific gravity. This makes it possible to carry out replacement of the sample solution without changing the buffer solution contained in the reservoir. Therefore, it is not necessary to waste the buffer solution, thereby reducing the consumption of the buffer solution.

Further, in the pretreatment method, by using, as the substrate, one having a solution supply channel for supplying a solution from the side of the reservoir, it is possible to introduce the sample solution through the solution supply channel in the sample introduction step. In this case, it is possible to more easily bring the sample solution into contact with the end surface of the capillary even when the amount of the sample solution is very small as compared to a case where the sample solution is introduced from above the reservoir. As a result, it is possible to reduce the amount of the sample to be used. This is particularly effective at analyzing a rare sample.

Further, by using such a substrate for analysis having a solution supply channel, it is possible to introduce the liquid for replacement through the solution supply channel in the sample replacement step. In this case, it is possible to more reliably replace the sample solution remaining in the reservoir, especially at the bottom of the reservoir with the liquid for replacement.

The pretreatment apparatus for electrophoresis according to the present invention can automatically perform the pretreatment method according to the present invention on the substrate held by the substrate holding unit. At this time, all an analyst has to do is to prepare liquids such as a sample solution and a buffer solution. Therefore, it is possible to replace the sample solution remaining in the reservoir after sample introduction into the capillary with the liquid for replacement without disturbing the reservoir-side end surface of the capillary. This makes it possible to reliably remove the sample remaining after sample introduction into the capillary from an area close to the end surface of the capillary and thereby to prevent the remaining sample from being newly introduced into the capillary during analysis so that analytical accuracy is improved.

DETAILED DESCRIPTION OF THE INVENTION

One embodiment of a pretreatment method of injecting a sample by an electrokinetic method for electrophoresis using a capillary plate will be described.

Figure 1A:
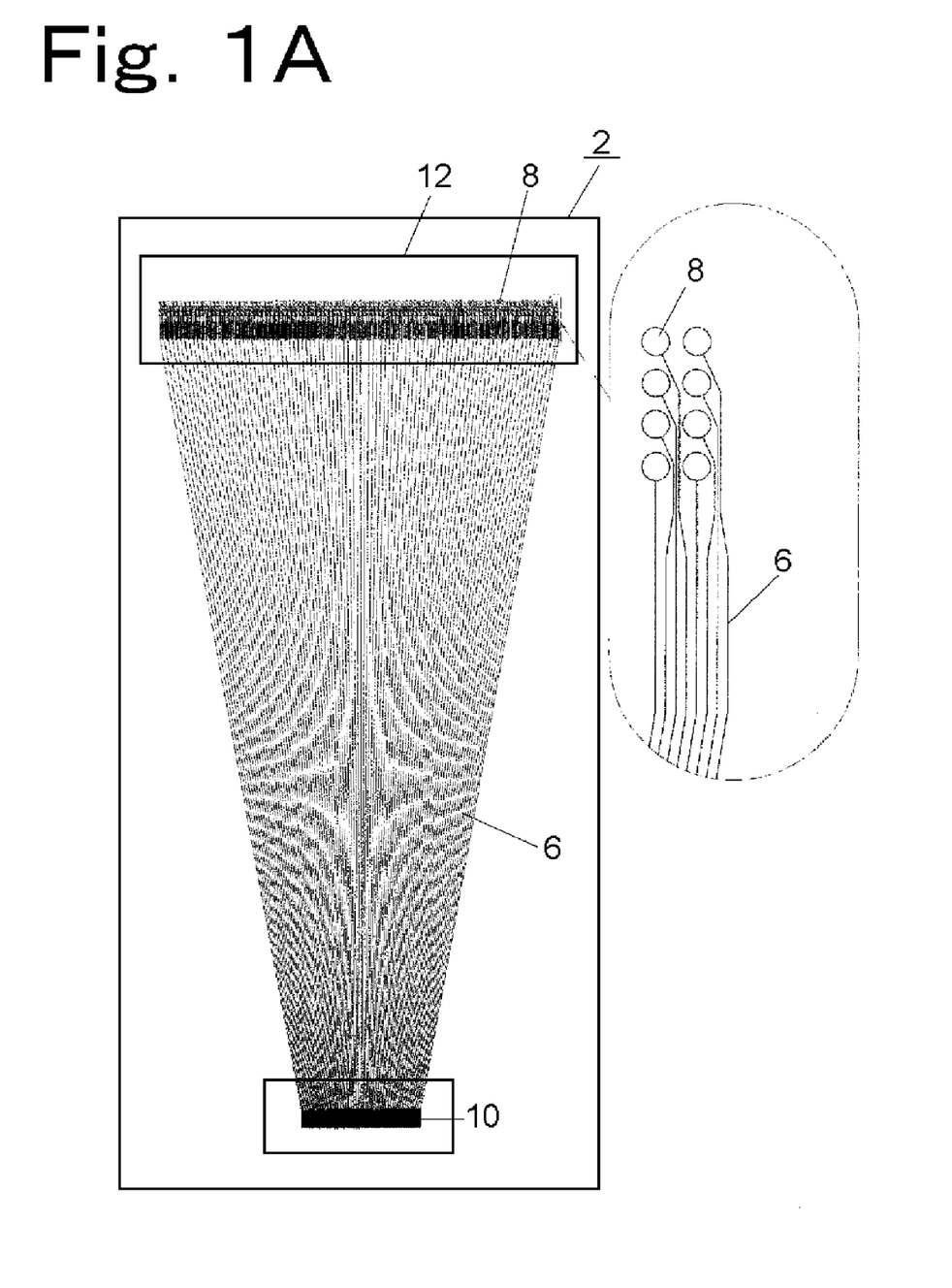
FIG. 1A shows a plan view of one example of a capillary plate and an enlarged detail view of an area enclosed with a chain double-dashed line in the plan view.
Figure 1B:
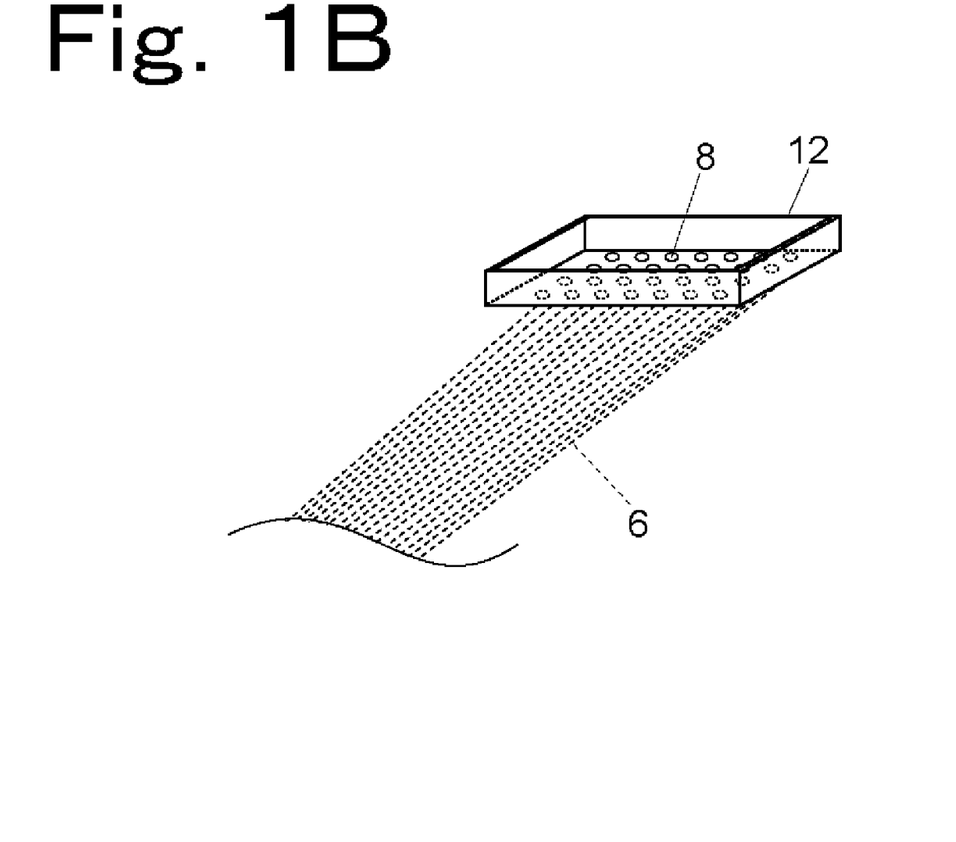
FIG. 1B is a perspective view of a cathode-side end portion of the capillary plate shown in FIG. 1A.
Figure 1C:
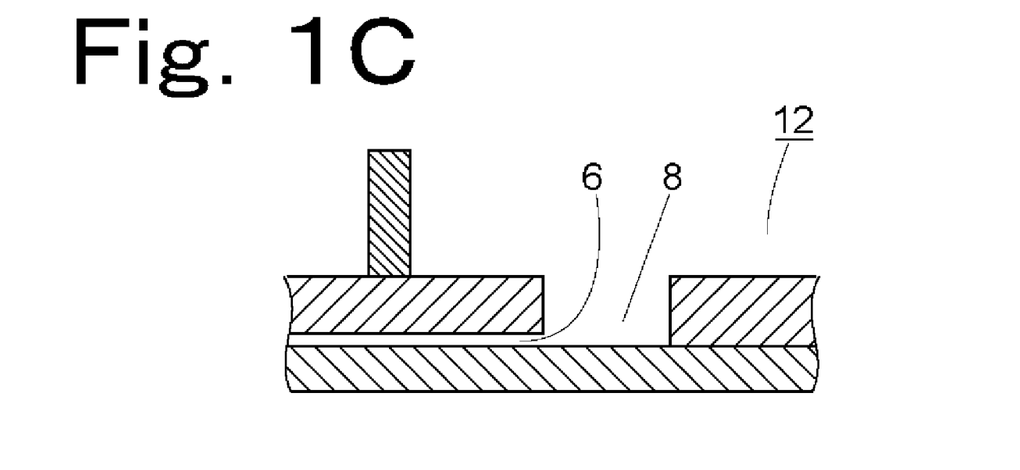
FIG. 1C is an enlarged sectional view of one sample reservoir in the cathode-side end portion of the capillary plate shown in FIG. 1A.

FIG. 1A shows a plan view of one example of a capillary plate and an enlarged detail view of an area enclosed with a chain double-dashed line in the capillary plate, FIG. 1B is a perspective view of a cathode-side end portion of the capillary plate shown in FIG. 1A, and FIG. 1C is an enlarged sectional view of one sample reservoir in the cathode-side end portion.

As shown in FIG. 1A, a capillary plate 2 to be used as a substrate for analysis in this embodiment has, in the inside thereof, a plurality of capillaries 6 as separation channels for separating a sample. On one end side (cathode side) of each of the capillaries 6, a sample reservoir 8 is provided as a sample injection portion. The other end (anode-side end) of each of the capillaries 6 is connected to a common reservoir 10 provided in the surface of the capillary plate 2.

On the cathode-side end portion of the capillary plate 2, a buffer reservoir 12 having a larger capacity than the sample reservoir 8 is provided. All the sample reservoirs 8 are arranged at the bottom of the buffer reservoir 12. As shown in FIG. 1C, the capillary 6 is connected to the side wall of the sample reservoir 8 at a position near the bottom of the sample reservoir 8.

Figure 2:
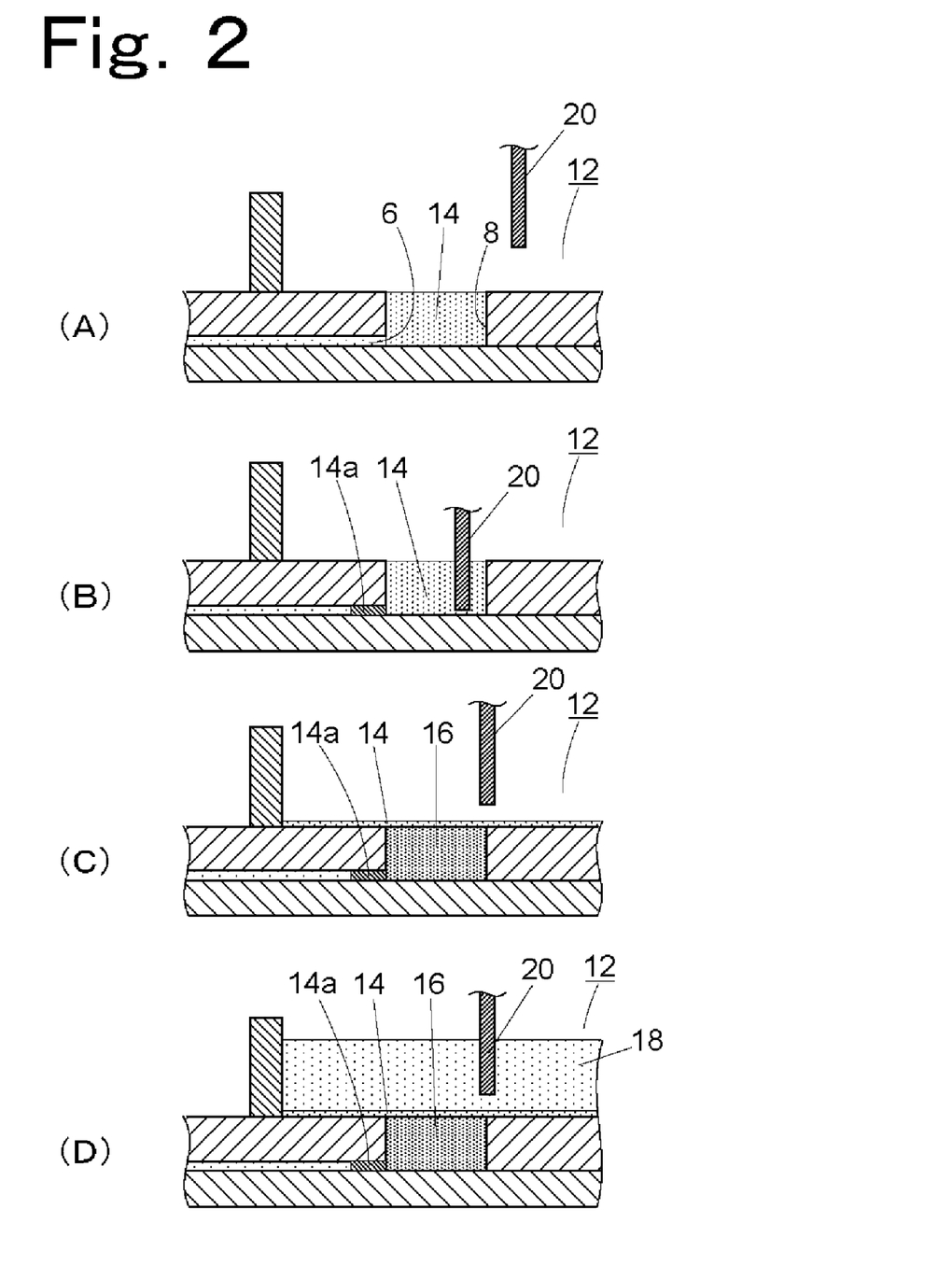

FIG. 2 is an enlarged sectional view of one of the sample reservoirs provided on the cathode-side end portion of the capillary plate for explaining the steps of pretreatment for electrophoretic analysis using the capillary plate shown in FIGS. 1A to 1C.

Pretreatment for electrophoretic analysis using the capillary plate 2 is as follows. A sample 14 is supplied into a sample reservoir 8 (see FIG. 2(A)). It is to be noted that at this time, a capillary 6 has already been filled with a separation medium. Then, a voltage is applied through an electrode 20 to introduce the sample into the capillary 6 (see FIG. 2(B)). Reference numeral 14a represents an end portion of the separation medium into which the sample has been introduced. A liquid 16 for replacement having a larger specific gravity than the sample 14 is supplied into the sample reservoir 8 to replace the sample 14 remaining in the sample reservoir 8 with the liquid 16 for replacement (see FIG. 2(C)). As such a liquid 16 for replacement, for example, a solution obtained by mixing ethylene glycol, 10×TTE (TRIS-TAPS-EDTA), and water at a ratio of 8:1:1 can be used. The liquid 16 for replacement needs to be supplied in an amount enough to remove the sample 14 remaining in the sample reservoir 8 from an area close to the end surface of the capillary 6, but the liquid 16 for replacement is preferably supplied in an amount sufficient to fill the sample reservoir 8 in order to facilitate treatment to be carried out after washing after electrophoresis.

Then, a buffer solution 18 is supplied into a buffer reservoir 12 (see FIG. 2(D)), and a voltage is applied to separate the sample introduced into the end portion 14a of the separation medium. In a case where the capillary plate is repeatedly used, a normal buffer solution not subjected to an increase in specific gravity is preferably supplied as the buffer solution 18 in order to facilitate washing to be carried out later.

According to the pretreatment method shown in FIG. 2, as shown in FIG. 2(C), since the liquid 16 for replacement having a larger specific gravity than the sample 14 is supplied into the sample reservoir 8 after the sample 14 is introduced into the capillary 6, it is possible to replace the sample 14 remaining in the sample reservoir 8 with the liquid 16 for replacement without disturbing the end surface of the separation medium contained in the capillary 6.

Conventionally, the sample 14 remaining in the sample reservoir 8 is removed by washing the sample reservoir 8 by way of a nozzle. However, it is difficult to completely remove the sample 14 remaining in the sample reservoir 8 by washing the sample reservoir 8 by way of a nozzle. If the sample 14 remains at the bottom of the sample reservoir 8, especially in the vicinity of the end surface of the capillary 6, it is likely that the remaining sample 14 will affect analysis.

On the other hand, according to the pretreatment method of this embodiment, it is possible to remove the sample 14 remaining in the sample reservoir 8, especially at the bottom of the sample reservoir 8 and thereby to prevent the sample 14 from being present near the end surface of the capillary 6. This makes it possible to prevent the remaining sample 14 from being introduced into the capillary 6 during electrophoretic analysis.

It is to be noted that in the pretreatment method according to this embodiment, at the time of supplying the liquid 16 for replacement into the sample reservoir 8, pipetting may be supplementarily carried out using a nozzle to repeat suction and discharge actions so that the sample 14 remaining at the bottom of the sample reservoir 8 will be more reliably replaced with the liquid 16 for replacement.

Figure 3:
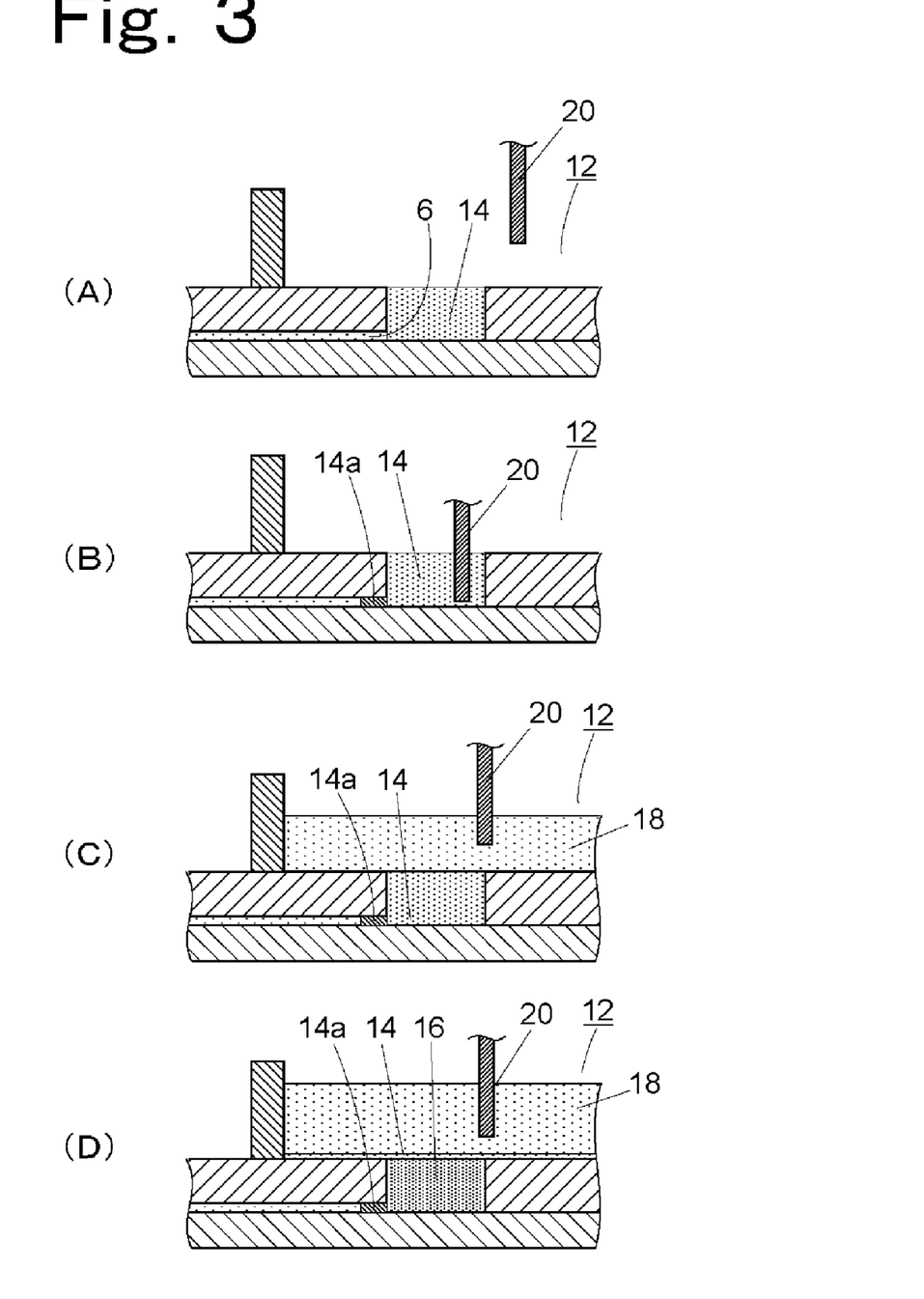

FIG. 3 is a sectional view showing the steps of another embodiment of the pretreatment method according to the present invention.

According to the pretreatment method of this embodiment, a sample 14 is supplied into a sample reservoir 8 (see FIG. 3(A)), a voltage is then applied through an electrode 20 to introduce the sample into the end portion of a capillary 6 filled with a separation medium (see FIG. 3(B)), and a buffer solution 18 is then supplied into a buffer reservoir 12 (see FIG. 3(C)). Then, a liquid 16 for replacement having a larger specific gravity than the sample 14 and the buffer solution 18 is supplied into the sample reservoir 8 to replace the sample 14 remaining in the sample reservoir 8 with the liquid 16 for replacement (see FIG. 3(D)).

As described above, the pretreatment method shown in FIG. 3 is different from the pretreatment method shown in FIG. 2 in that the buffer solution 18 is supplied into the buffer reservoir 12 to fill the sample reservoir 8 and the buffer reservoir 12 with the buffer solution 18 after the sample is introduced into the capillary 6 filled with the separation medium but before the liquid 16 for replacement is supplied into the sample reservoir 8. By supplying the liquid 16 for replacement having a larger specific gravity than the sample 14 and the buffer solution 18 into the sample reservoir 8, the sample 14 remaining in the sample reservoir 8 is replaced with the liquid 16 for replacement due to their difference in specific gravity so that the sample 14 is replaced on the liquid 16 for replacement. As described above, even when the liquid 16 for replacement is supplied into the sample reservoir 8 after the buffer reservoir 12 is filled with the buffer solution 18, it is possible to replace the sample 14 remaining in the sample reservoir 8 with the liquid 16 for replacement and thereby possible to remove the remaining sample 14 from an area close to the end surface of the capillary 6 without disturbing the end surface of the separation medium charged in the capillary 6.

It is to be noted that also in the case of the pretreatment method according to this embodiment, pipetting may be supplementarily carried out using a nozzle to repeat suction and discharge actions so that the sample 14 remaining in the sample reservoir 8, especially at the bottom of the sample reservoir 8 will be more reliably replaced with the liquid 16 for replacement.

Figure 4:
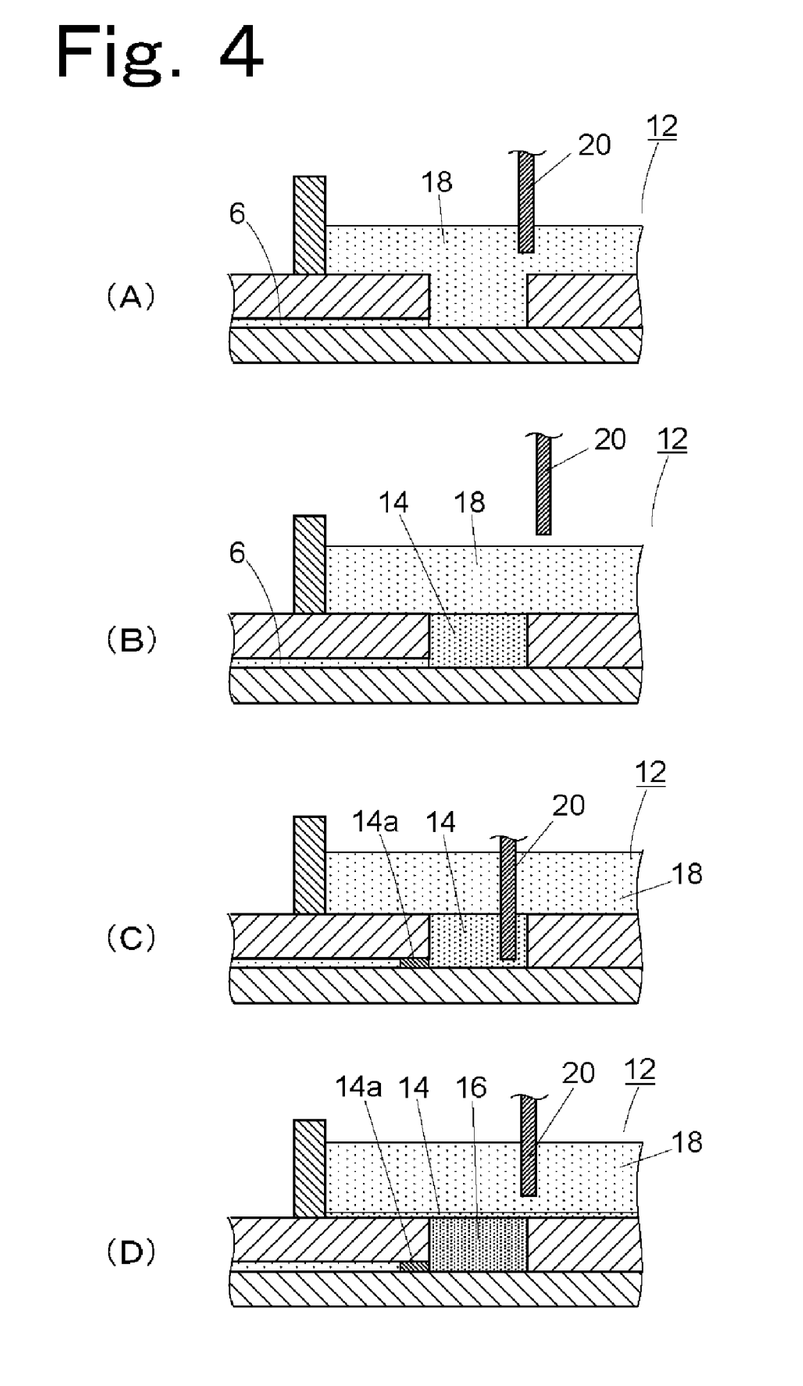

Hereinbelow, yet another embodiment of the pretreatment method according to the present invention will be described. FIG. 4 is a sectional view showing the steps of yet another embodiment of the pretreatment method according to the present invention.

In a state where a capillary 6 is filled with a separation medium, a buffer solution 18 is first supplied into a sample reservoir 8 and a buffer reservoir 12, and then a preliminary run is carried out (see FIG. 4(A)). A preliminary run is carried out by applying electric power before sample injection in order to remove impurity ions from the separation medium contained in the capillary. Then, a sample solution using, as a solvent, a liquid having a larger specific gravity than the buffer solution 18 is supplied as a sample 14 into the sample reservoir 8 (see FIG. 4(B)). The sample 14 has a larger specific gravity than the buffer solution 18, and therefore penetrates the buffer solution 18 and then fills the sample reservoir 8. In this state, a voltage is applied through an electrode 20 to introduce the sample into the end portion of the separation medium (see FIG. 4(C)). Then, a liquid 16 for replacement having a larger specific gravity than the sample 14 is supplied into the sample reservoir 8 to replace the sample 14 remaining in the sample reservoir 8 with the liquid 16 for replacement (see FIG. 4(D)).

According to the pretreatment method of this embodiment, since the sample 14 using, as a solvent, a liquid having a larger specific gravity than the buffer solution 18 is supplied into the sample reservoir 8 in a state where the sample reservoir 8 and the buffer reservoir 12 are filled with the buffer solution 18, it is possible to introduce the sample 14 into the capillary 6 while the sample 14 is prevented from being dried. Also in the case of the pretreatment method according to this embodiment, since the sample 14 remaining in the sample reservoir 8 is replaced with the liquid 16 for replacement, it is possible to remove the remaining sample 14 from an area close to the end surface of the capillary 6 without disturbing the end surface of the separation medium charged in the capillary 6.

According to a conventional method, even in a case where the sample 14 using, as a solvent, a liquid having a larger specific gravity than the buffer solution 18 is supplied into the sample reservoir 8 in a state where the sample reservoir 8 and the buffer reservoir 12 are filled with the buffer solution 18, the buffer solution 18 is once removed from the sample reservoir 8 and the buffer reservoir 12 after the sample is introduced into the capillary 6 in order to remove the sample 14 remaining in the sample reservoir 8. In this case, it is necessary to refill the sample reservoir 8 and the buffer reservoir 12 with the buffer solution 18 after washing the sample reservoir 8. However, according to the pretreatment method of this embodiment, it is possible to remove the sample 14 remaining in the sample reservoir 8 from an area close to the end surface of the capillary 6 by replacement without changing the buffer solution 18 and thereby to reduce the consumption of the buffer solution 18.

It is to be noted that also in the case of the pretreatment method according to this embodiment, pipetting may be supplementarily carried out using a nozzle to repeat suction and discharge actions so that the sample 14 remaining in the sample reservoir 8, especially at the bottom of the sample reservoir 8 will be more reliably removed.

The pretreatment methods shown in FIGS. 2 to 4 can be used not only for the capillary plate 2 shown in FIG. 1 but also for various substrates for analysis such as a microchip in which one capillary is formed in one substrate and the like.

Figure 5:
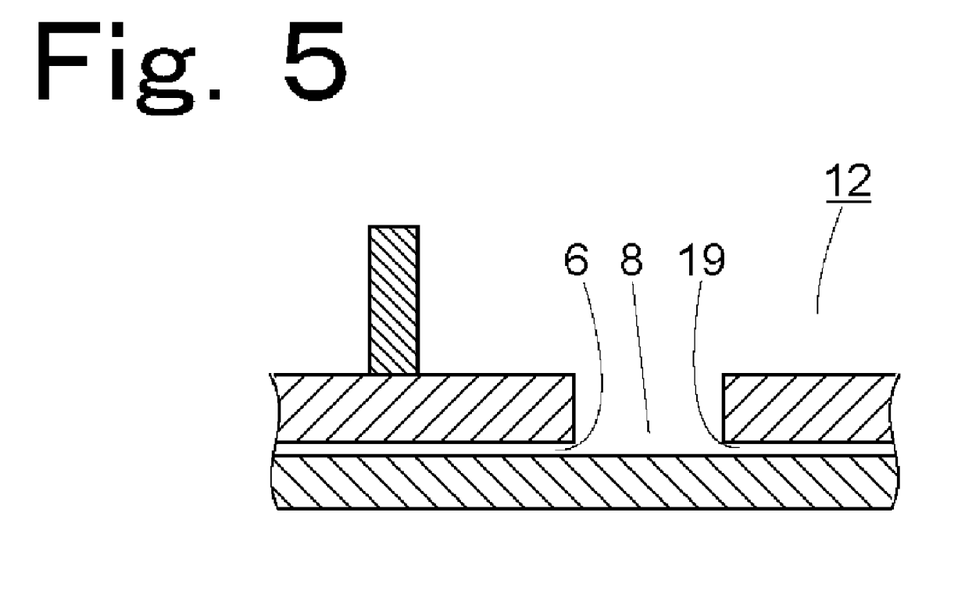
FIG. 5 is an enlarged sectional view of the cathode-side end portion of a substrate for analysis according to one embodiment of the present invention.

One embodiment of a substrate for analysis suitable for use in the pretreatment method according to the present invention is shown in FIG. 5. FIG. 5 is an enlarged sectional view of a cathode-side end portion of the substrate for analysis according to the embodiment of the present invention.

This substrate for analysis has capillaries 6 for separating samples, sample reservoirs 8 each connected to the cathode-side end portion of one of the capillaries 6, and a buffer reservoir 12 common to the plurality of sample reservoirs 8. The capillaries 6 are filled with a separation medium before use. Further, a solution supply channel 19, through which a solution can be supplied from the side of the sample reservoir 8, is provided at a position different from that of the capillary 6.

Figure 6:
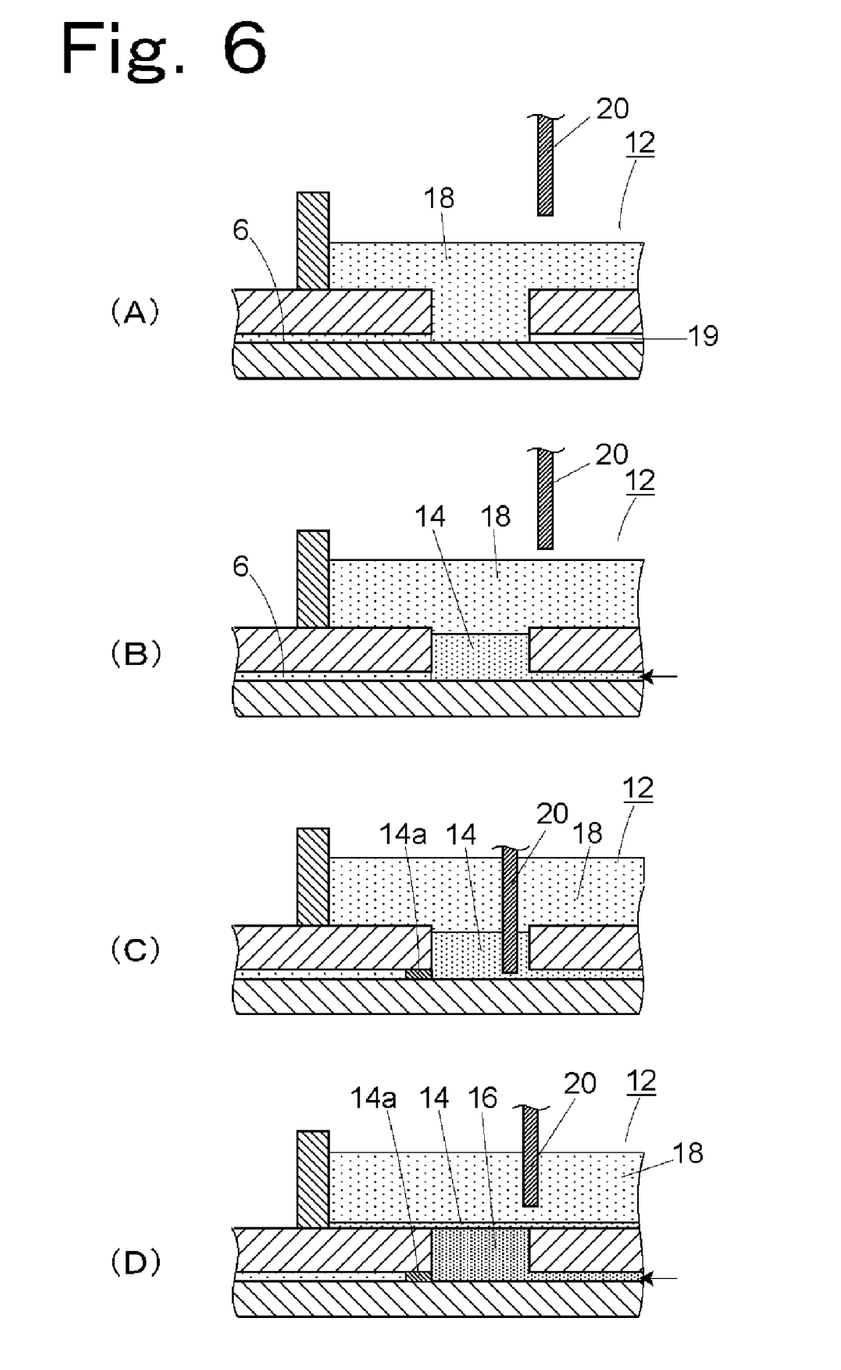

FIG. 6 is an enlarged sectional view showing the steps of one example of a method for pretreatment of electrophoretic analysis using the substrate for analysis shown in FIG. 5.

According to this pretreatment method, a capillary 6 is filled with a separation medium, and then a buffer solution 18 is first supplied into a sample reservoir 8 and a buffer reservoir 12 (see FIG. 6(A)). Then, a sample 14 using, as a solvent, a liquid having a larger specific gravity than the buffer solution 18 is supplied into the sample reservoir 8 through the solution supply channel 19 (see FIG. 6(B)). Then, a voltage is applied through an electrode 20 to introduce the sample into the end portion of the separation medium (see FIG. 6(C)). Then, a liquid 16 for replacement having a larger specific gravity than the sample 14 is introduced through the solution supply channel 19 to replace the sample 14 remaining in the sample reservoir 8 with the liquid 16 for replacement (see FIG. 6(D)).

According to this pretreatment method, since the sample 14 is supplied from the side of the sample reservoir 8 through the solution supply channel 19, it is possible to reliably bring the sample 14 into contact with the end surface of the capillary 6 and thereby to reduce the amount of the sample 14 to be supplied. Further, by supplying the liquid 16 for replacement near the bottom of the sample reservoir 8 through the solution supply channel 19, it is possible to push the sample 14 remaining in the sample reservoir 8 upward from the bottom side of the sample reservoir 8 and thereby to reliably replace the sample 14 remaining at the bottom of the sample reservoir 8 with the liquid 16 for replacement.

It is to be noted that according to this pretreatment method, the liquid 16 for replacement is supplied through the solution supply channel 19, but the present invention is not limited thereto. For example, the liquid 16 for replacement may be supplied by discharging it from a nozzle while the sample 14 is supplied through the solution supply channel 19. Also in the case of using the substrate for analysis shown in FIG. 6, the sample 14 may be supplied in a state where the sample reservoir 8 is not filled with the buffer solution 18 as in the case of the embodiment shown in FIG. 2 or 3.

The pretreatment methods shown in FIGS. 2 to 5 may be automatically carried out using an apparatus. Examples of such an apparatus include apparatuses dedicated to pretreatment and electrophoresis apparatuses equipped with a pretreatment system.

Figure 7:
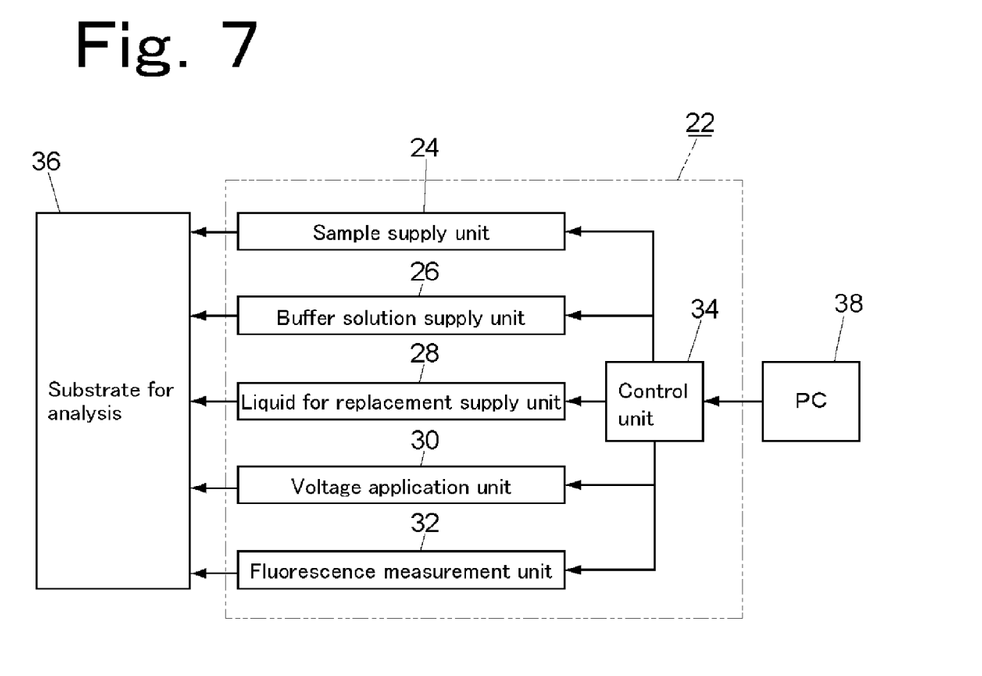
FIG. 7 is a block diagram showing one embodiment of an electrophoresis analyzer for carrying out operations from pretreatment to electrophoretic analysis.

FIG. 7 is a block diagram showing one embodiment of an electrophoresis analyzer for carrying out operations from pretreatment to electrophoretic analysis.

An electrophoresis analyzer 22 includes a sample supply unit 24 for supplying samples, previously prepared and set at predetermined positions by an analyst, into sample reservoirs of a substrate 36 for analysis, a buffer solution supply unit 26 for delivering a buffer solution to supply it into buffer reservoirs of the substrate 36, a liquid for replacement supply unit 28 for supplying a liquid (liquid for replacement) having a larger specific gravity than the samples and the buffer solution, a voltage application unit 30 for applying a voltage to the reservoirs of the substrate 36 through electrodes to introduce the samples into capillaries of the substrate 36 for analysis and to carry out electrophoretic separation of the samples introduced into the capillaries, a fluorescence measurement unit 32 for detecting sample components separated by electrophoresis in the capillaries, and a control unit 34 for controlling the operations of the sample supply unit 24, buffer solution supply unit 26, liquid for replacement supply unit 28, voltage application unit 30, and fluorescence measurement unit 32.

Further, the control unit 34 is connected to a personal computer (PC) 38 so that an analyst can operate the electrophoresis analyzer 22 while watching a monitor.

Each of the sample supply unit 24, buffer solution supply unit 26, and liquid for replacement supply unit 28 has a tank for storing a liquid such as a sample, a buffer solution, or a liquid for replacement, a liquid delivery pump for delivering such a liquid, or the like.

Each of the sample supply unit 24, buffer solution supply unit 26, and liquid for replacement supply unit 28 may be connected to a movable nozzle so that a liquid such as a sample, a buffer solution, or a liquid for replacement will be supplied by moving the nozzle to a predetermined position. In a case where the substrate for analysis having a solution supply channel 19 for supplying a liquid from the side of a sample reservoir 8 (e.g., the substrate for analysis shown in FIG. 5) is used, the sample supply unit 24 may be connected to the solution supply channel 19 so that a sample will be supplied into the sample reservoir 8 from the side of the sample reservoir 8. Alternatively, the sample supply unit 24 and the liquid for replacement supply unit 28 may be connected to the solution supply channel 19 via a channel switching valve or the like so that a liquid such as a sample or a liquid for replacement will be supplied into the sample reservoir 8 through the solution supply channel 19.

The control unit 34 performs, for example, the following control actions. It is to be noted that a capillary of a substrate for analysis is previously filled with a separation medium before the control unit 34 begins to perform control actions.

(Control 1)

First, the control unit 34 allows the sample supply unit 24 to supply a sample into a sample reservoir of a substrate for analysis, and then allows the voltage application unit 30 to apply a voltage through electrodes to introduce a part of the sample into a capillary. Next, the control unit 34 allows the liquid for replacement supply unit 28 to supply a liquid for replacement into the sample reservoir. Then, the control unit 34 allows the buffer solution supply unit 26 to supply a buffer solution, and then allows the voltage application unit 26 to apply a voltage through given electrodes to subject the sample to electrophoretic separation in the capillary. Last, the control unit 34 allows the fluorescence measurement unit 32 to detect sample components separated by electrophoresis in the capillary and then to send measurement data to the PC 38.

(Control 2)

The control unit 34 allows the sample supply unit 24 to supply a sample into a sample reservoir of a substrate for analysis, and then allows the voltage application unit 30 to apply a voltage through electrodes to introduce a part of the sample into a capillary. Next, the control unit 34 allows the buffer solution supply unit 26 to supply a buffer solution into a buffer reservoir of the substrate for analysis. In a state where the buffer reservoir is filled with the buffer solution, the control unit 34 allows the liquid for replacement supply unit 28 to supply a liquid for replacement into the sample reservoir. Then, the control unit 34 allows the voltage application unit 26 to apply a voltage through given electrodes to subject the sample to electrophoretic separation in the capillary. Last, the control unit 34 allows the fluorescence measurement unit 32 to detect sample components separated by electrophoresis in the capillary and then to send measurement data to the PC 38.

(Control 3)

In order to allow the control unit 34 to perform this control method, an analyst previously charges, into the sample supply unit 24, a sample solution using, as a solvent, a liquid having a larger specific gravity than a buffer solution to be supplied from the buffer solution supply unit 26.

The control unit 34 allows the buffer solution supply unit 26 to supply a buffer solution into a buffer reservoir of a substrate for analysis. Then, the control unit 34 allows the voltage application unit 30 to perform a preliminary run, and then allows the sample supply unit 24 to supply the sample solution into a sample reservoir of the substrate for analysis. Then, the control unit 34 allows the voltage application unit 30 to apply a voltage through electrodes to introduce the sample into the end portion of a separation medium contained in a capillary. Next, the control unit 34 allows the liquid for replacement supply unit 28 to supply a liquid for replacement into the sample reservoir. Then, the control unit 34 allows the voltage application unit 26 to apply a voltage through given electrodes to subject the sample to electrophoretic separation in the capillary. Last, the control unit 34 allows the fluorescence measurement unit 32 to detect sample components separated by electrophoresis in the capillary and then to send measurement data to the PC 38.

By allowing the control unit 34 to carry out any one of the control methods described above with reference to (Control 1) to (control 3), operations from pretreatment to analysis are automatically performed by the electrophoresis analyzer. At this time, all an analyst has to do is to prepare a sample, a buffer solution and a liquid for replacement, and set these liquids to their respective predetermined positions.

In the case of using a conventional apparatus, after a sample is introduced into a capillary of a substrate for analysis, a sample reservoir cannot be sufficiently washed without disturbing the end surface of a separation medium in the capillary facing the sample reservoir. However, since the apparatus according to this embodiment has a liquid for replacement supply unit 28 so that a liquid for replacement having a larger specific gravity than a sample will be automatically introduced into a sample reservoir from the liquid for replacement supply unit 25 after the sample is introduced into a capillary, it is possible to remove the remaining sample from the sample reservoir without disturbing the end surface of a separation medium contained in the capillary.

It is to be noted that in a case where a system such as a liquid for replacement supply unit 28 used in (Control 1) to (Control 3) has a nozzle capable of sucking and discharging a liquid, pipetting may be carried out using the nozzle after a liquid for replacement is supplied into a sample reservoir from the liquid for replacement supply unit 28.

Figure 8:
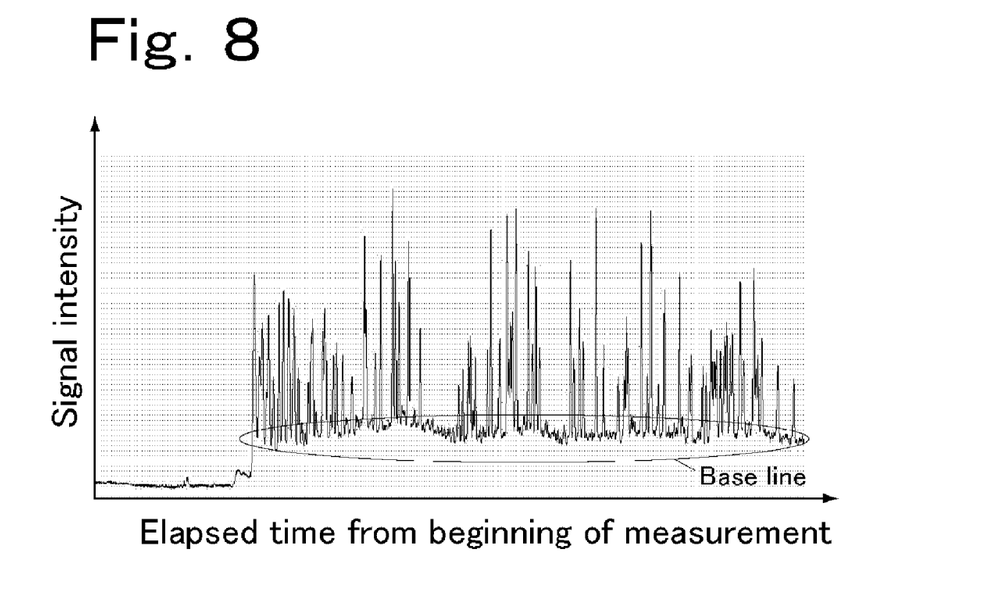
FIG. 8 is a graph showing elapsed time from the beginning of measurement and signal intensity measured by a fluorescence measurement unit of the electrophoresis analyzer.
Figure 9:
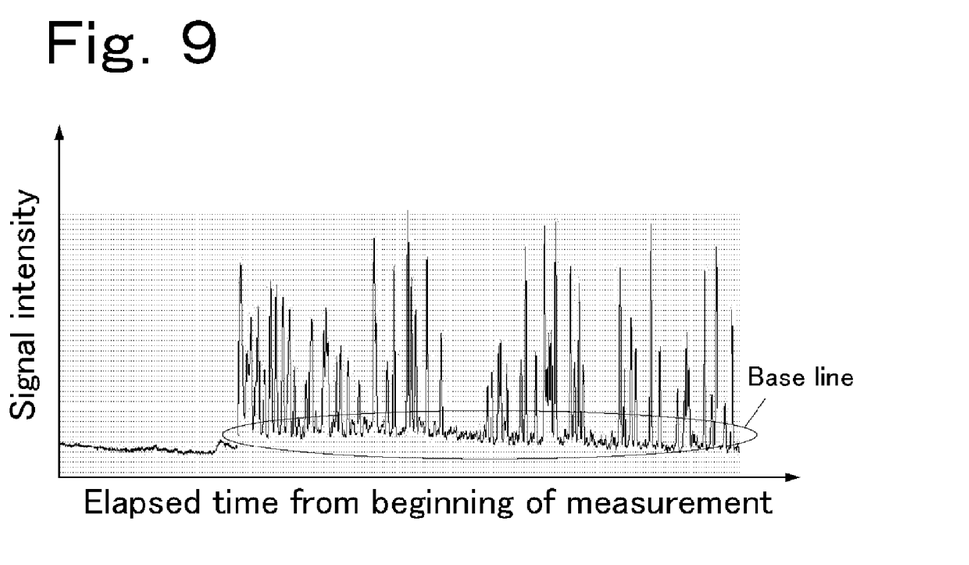
FIG. 9 is a graph showing elapsed time from the beginning of measurement and signal intensity measured by a fluorescence measurement unit of the electrophoresis analyzer.
Figure 10:
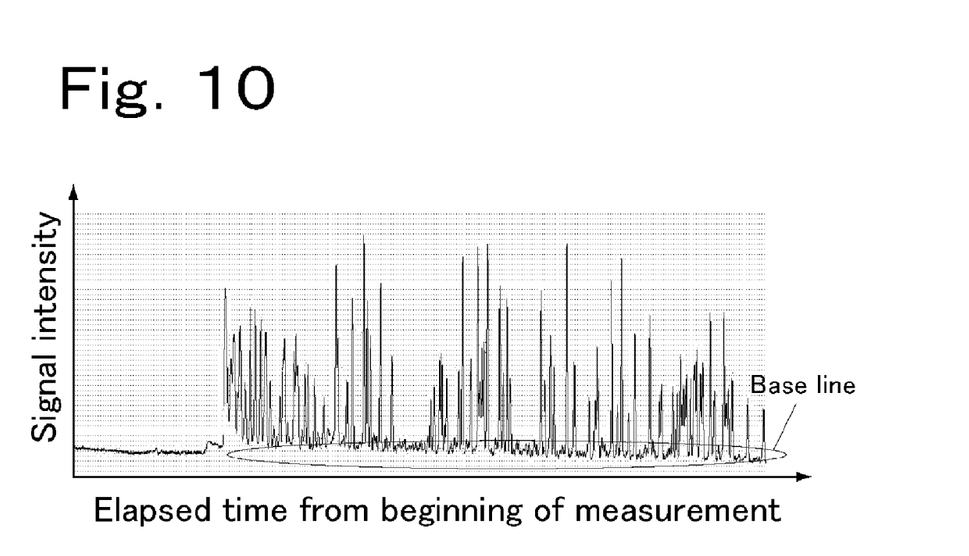
FIG. 10 is a graph showing elapsed time from the beginning of measurement and signal intensity measured by a fluorescence measurement unit of the electrophoresis analyzer.

FIGS. 8, 9, and 10 are graphs showing elapsed time from the beginning of measurement by the fluorescence measurement unit 32 of the electrophoresis analyzer 22 shown in FIG. 7 and signal intensity. In each of the graphs, the horizontal axis represents elapsed time from the beginning of measurement and the vertical axis represents signal intensity.

In this measurement, a plate having a structure shown in FIG. 2 was used. More specifically, the plate had one flow channel, and a sample reservoir 8 had a capacity of 3 μL. As a sample, one obtained by dissolving a reaction product ethanol-purified using BigDye® Terminator V3.1 Cycle Sequencing Kit (Applied Biosystems) in a dissolving liquid containing 50% ethylene glycol was used. As a buffer solution, 50 mM Tris/50 mM TAPS/2 mM EDTA was used. A liquid for replacement to be supplied from the liquid for replacement supply unit 28 had a composition of ethylene glycol:10×TTE:water=8:1:1.

Pretreatment for the measurement was as follows. The sample was supplied into the sample reservoir 8, and then a voltage was applied to introduce the sample into a capillary 6. In the case of measurement shown in FIG. 8, after the sample was introduced into the capillary 6, the buffer solution was supplied into a buffer reservoir 12 without supplying the liquid for replacement into the sample reservoir, and then analysis was carried out. In the case of measurement shown in FIG. 9, after the sample was introduced into the capillary 6, the sample remaining in the sample reservoir 8 was replaced with 6 μL of the liquid for replacement supplied from the liquid for replacement supply unit 28 into the sample reservoir 8, the buffer solution was supplied into the buffer reservoir 12, and then analysis was carried out. In the case of measurement shown in FIG. 10, after the sample was introduced into the capillary 6, 6 μL of the liquid for replacement was supplied from the liquid for replacement supply unit 28 into the sample reservoir 8, pipetting was performed using a nozzle in the sample reservoir 8 to the extent that the end surface of a separation medium charged in the capillary 6 was not disturbed, the buffer solution was supplied into the buffer reservoir 12, and then analysis was carried out.

In the case of measurements shown in FIGS. 8, 9, and 10, as can be seen from the measurement result shown in FIG. 8, the base line of signal intensity is not stable after a fluorescence detection signal begins to be detected. This is caused by introduction of the sample remaining in the sample reservoir 8 into the capillary 6 during measurement.

On the other hand, as can be seen from the measurement result shown in FIG. 9, the base line of signal intensity is stable after a fluorescence detection signal begins to be detected. This is because the sample remaining in the sample reservoir 8 has been removed from an area close to the end surface of the capillary 6 by replacing the sample in the sample reservoir 8 with the liquid for replacement so that the sample is less likely to be introduced into the capillary 6 during measurement.

Further, as can be seen from the measurement result shown in FIG. 10, the base line of signal intensity is more stable than that shown in FIG. 9 after a fluorescence detection signal begins to be detected. From the result, it has been found that the efficiency of replacing the sample remaining in the sample reservoir 8, especially at the bottom of the sample reservoir 8 with the liquid for replacement supplied into the sample reservoir 8 after sample introduction into the capillary 6 can be further improved by supplementarily carrying out pipetting.

BRIEF DESCRIPTION OF THE DRAWINGS

FIG. 2(A) to FIG. 2(D) are enlarged sectional views of one sample reservoir in the cathode-side end portion of the capillary plate for explaining the steps of pretreatment for electrophoretic analysis using the capillary plate.

FIG. 3(A) to FIG. 3(D) are enlarged sectional views showing the steps of another embodiment of the method for pretreatment of electrophoretic analysis using the capillary plate 2.

FIG. 4(A) to FIG. 4(D) are enlarged sectional views showing the steps of yet another embodiment of the method for pretreatment of electrophoretic analysis using the capillary plate 2.

FIG. 6(A) to FIG. 6(D) are enlarged sectional views showing the steps of one example of the method for pretreatment of electrophoretic analysis using the substrate for analysis shown in FIG. 5.

DESCRIPTION OF THE REFERENCE NUMERALS 2 capillary plate
6 capillary
8 cathode-side sample reservoir
10 anode-side reservoir
12 cathode-side buffer reservoir
14 sample
14a introduced sample
16 liquid for replacement
18 buffer solution
19 solution supply channel
20 electrode
22 electrophoresis analyzer
24 sample supply unit
26 buffer solution supply unit
28 liquid for replacement supply unit
30 voltage application unit
32 fluorescence measurement unit
34 control unit
36 substrate for analysis

What is claimed is:

1. A method for pretreatment of electrophoretic analysis using a substrate for analysis having a capillary for separating a sample and a reservoir provided at the end portion of the capillary to introduce a sample into the capillary, the method comprising:

a sample introduction step for supplying a sample into the reservoir followed by applying a voltage to introduce the sample into the capillary; and a sample replacement step for introducing a liquid for replacement having a larger specific gravity than the sample into the reservoir to remove the sample remaining in the reservoir from the reservoir before an electrophoretic separation step for subjecting the sample to electrophoretic separation.

2. The pretreatment method according to claim 1,
wherein in the sample introduction step, a buffer solution is supplied into the reservoir prior to supplying the sample, and
wherein the sample is a solution having a solvent having a larger specific gravity than the buffer solution.

3. The pretreatment method according to claim 2,
wherein the substrate has a solution supply channel for supplying a solution from the side of the reservoir, and
wherein in the sample introduction step, the sample solution is introduced through the solution supply channel.

4. The pretreatment method according, to claim 2,
wherein the substrate has a solution supply channel for supplying a solution from the site of the reservoir, and
wherein in the sample replacement step, the liquid for replacement is introduced through the solution supply channel.

5. The pretreatment method according to claim 3,
wherein in the sample replacement step, the liquid for replacement is introduced through the solution supply channel.

* * * * *